(12) United States Patent
Suri et al.

(10) Patent No.: US 7,942,060 B2
(45) Date of Patent: May 17, 2011

(54) UNIVERSAL ULTRASOUND HOLDER AND ROTATION DEVICE

(75) Inventors: Jasjit Suri, Roseville, CA (US); Kanwar Suri, Thousand Oaks, CA (US); Animesh Khemka, Grass Valley, CA (US); Dinesh Kumar, Grass Valley, CA (US)

(73) Assignee: Eigen, Inc., Grass Valley, CA (US)

( * ) Notice: Subject to any disclaimer, the term of this patent is extended or adjusted under 35 U.S.C. 154(b) by 1086 days.

(21) Appl. No.: 11/691,150

(22) Filed: Mar. 26, 2007

(65) Prior Publication Data

US 2008/0221453 A1  Sep. 11, 2008

Related U.S. Application Data

(60) Provisional application No. 60/893,317, filed on Mar. 6, 2007, provisional application No. 60/894,602, filed on Mar. 13, 2007.

(51) Int. Cl.
*G01N 29/22* (2006.01)
*G01N 29/04* (2006.01)
*G01N 29/26* (2006.01)
*A61B 8/00* (2006.01)
*A61B 8/13* (2006.01)

(52) U.S. Cl. .............. 73/661; 73/618; 73/644; 600/445; 600/459

(58) Field of Classification Search ............... 73/618, 73/620, 622, 644, 661, 866.5; 600/445–446, 600/459
See application file for complete search history.

(56) References Cited

U.S. PATENT DOCUMENTS

| | | | |
|---|---|---|---|
| 3,002,375 A * | 10/1961 | Moffatt et al. | 73/640 |
| 3,415,548 A * | 12/1968 | Goodman et al. | 403/261 |
| 5,427,108 A * | 6/1995 | Bollinger | 600/461 |
| 5,487,388 A * | 1/1996 | Rello et al. | 600/445 |
| 5,971,929 A * | 10/1999 | Sakamoto et al. | 600/462 |
| 6,454,781 B1 * | 9/2002 | Witt et al. | 606/169 |
| 6,752,753 B1 * | 6/2004 | Hoskins et al. | 600/7 |
| 7,244,234 B2 * | 7/2007 | Ridley et al. | 600/459 |
| 7,472,615 B2 * | 1/2009 | Mayeaux | 73/866.5 |
| 7,475,602 B2 * | 1/2009 | Molenaar et al. | 73/866.5 X |
| 2008/0064960 A1 * | 3/2008 | Whitmore et al. | 600/459 |
| 2009/0145249 A1 * | 6/2009 | Dubbeldam et al. | 73/866.5 |
| 2010/0036245 A1 * | 2/2010 | Yu et al. | 600/439 |

* cited by examiner

*Primary Examiner* — Thomas P Noland
(74) *Attorney, Agent, or Firm* — Marsh Fischmann & Breyfogle LLP

(57) ABSTRACT

Provided herein are devices and methods for mounting variously configured medical imaging probes for imaging applications. In one aspect, a holding device allows for interfacing/holding most conventional ultrasound probes such that the probes may be attached to a positioning device using a common interface. As ultrasound probes come in various sizes and lengths, the device may adjust to different lengths, widths and shapes of different probes. Hence, the device may work in a substantially universal manner while securely holding probes with little wobble or other problems.

17 Claims, 14 Drawing Sheets

2D Image Storage

3D Volume Image

UNIVERSAL ULTRASOUND HOLDER AND ROTATION DEVICE

CROSS-REFERENCE TO RELATED APPLICATION

This application claims priority under 35 U.S.C. 119 to U.S. Provisional Application No. 60/893,317, entitled: "UNIVERSAL HOLDER," filed on Mar. 6, 2007, and No. 60/894,602, entitled: "CRADLE WITH MANUAL RATCHET," filed on Mar. 13, 2007, the contents of which are incorporated herein as if set forth in full.

FIELD OF INVENTION

The present invention is directed to an apparatus for holding and positioning a medical imaging instrument. More particularly, the invention relates to an apparatus adapted to hold a plurality of differently configured medical imaging instruments such that those instruments may be secured and/or rotated about at least one fixed axis.

BACKGROUND OF THE INVENTION

Medical imaging instruments are often utilized by doctors and other medical professionals to conduct non-invasive examinations. That is, medical imaging instruments, including X-ray, magnetic resonance (MR), computed tomography (CT), ultrasound, and various combinations of these instruments/techniques are utilized to provide images of internal patient structure for diagnostic purposes as well as for interventional procedures. Such medical imaging instruments allow examination of internal tissue that is not readily examined during normal visual or tactile examination. Applications include imaging in the areas of urology and brachytherapy.

Medical imaging devices typically allow for generating 3-D images of internal structures of interest. Such 3-D imaging may improve the accuracy and/or reliability of medical diagnosis. For instance, a medical imaging device may be utilized to generate a 3-D model or map of the prostate such that one or more biopsies may be taken from a desired location of the prostate. For purposes of prostrate imaging, image acquisition and guidance may be provided by a transrectal ultrasound-imaging device (TRUS). In such an application, the ultrasound-imaging device may be inserted into the rectum of a patient to generate an image. Such images may be utilized to take one or more biopsies from a prostate location of interest and/or implant radioactive seeds at one or more desired locations in a brachytherapy procedure.

In order to generate 3-D images, many medical imaging devices obtain a plurality of images (e.g., two dimensional images) and register these images together to form a 3-D image. Accordingly, movement of a medical imaging device between the acquisition of individual images makes it more difficult to properly align (e.g., register) the different images for purposes of generating accurate 3-D images.

Traditionally, having a medical practitioner manipulate the medical imaging instrument by hand has controlled medical instrument positioning for medical image acquisition and/or treatment, including that of ultrasound probes. That is, the medical practitioner manually guides the instrument. Such manual manipulation is suitable for many medical procedures. However, in instances where it is desirable to obtain multiple images for 3-D image generation, manual manipulation of the device may result in movement between images. Further, for biopsy and other treatment procedures it is desirable that the relative location between an imaging instrument and a tissue area of interest be known. That is, it is important that the device directs an imaging field to a particular tissue location and remain stationary to allow for guiding a biopsy/treatment device to a tissue location within the imaging field. Relative movement between the imaging device and the tissue area of interest during imaging and/or biopsy/treatment may impede the successful performance of these procedures.

Accordingly, a number of holding and manipulating/positioning assemblies have been proposed wherein a holder interfaces with an imaging device such as an ultrasound probe. Such a holder is then interconnected to one or more mechanical armatures and/or actuators such that the probe may be mechanically positioned and/or rotated. However, original equipment manufactures (OEMs) of ultrasound probes do not have a standardized design. As will be appreciated, ultrasound probes generated by different manufactures come in different lengths and widths. This is true for both the insertion portion end of a probe as well as a handle portion of the probe. This has resulted in the need for specialized holders and/or specialized positioning assemblies for differently configured ultrasound probes. Accordingly, prior positioning assemblies have required that a medical facility utilize a particular probe with a particular positioning assembly. Further, such positioning assemblies have typically been complicated and mechanically cumbersome.

SUMMARY OF THE INVENTION

Provided herein are devices and methods for the use of such devices for mounting variously configured medical imaging probes for imaging applications. Further, systems and methods are provided for acquiring medical images. In one aspect, a device allows for interfacing/holding most conventional ultrasound probes such that the probes may be attached to a positioning device using a common interface. As ultrasound probes come in various sizes and lengths, the device may adjust to different lengths, widths and shapes of different probes. Hence, the device may work in a substantially universal manner while securely holding probes with little wobble or other problems. The device may also be lightweight and compact to allow it to be used efficiently. The device may also allow use of a biopsy needle and/or a histological gun while a probe is held within the device.

In another aspect, the device may be utilized with a manual or automated (e.g., robotic) positioning/rotation device. The positioning/rotation device allows for axial misalignment correction for non-concentric probes to facilitate rotation around the axis of the probe tip. In a further aspect, the positioning/rotation device includes an assembly to allow accurate sampling even during manual rotation by a user.

Accordingly, provided herein is an apparatus that allows for interfacing with a plurality of differently configured ultrasound probes. The device includes a clamp body for receiving a portion of the ultrasound probe where the clamp body includes a first body member and a second body member that is moveably attached to the first body member. In this regard, the first and second body members are adapted to move between an open position and a closed position. At least one bias force member is disposed on the surface of one of the first and second body members. A mounting element is also associated with the surface of the clamp body. Such a mounting element allows for mounting the clamp body and, hence, a supported ultrasound probe to a positioning device.

Generally, the inclusion of a bias force member on a surface between the first and second body members allows the bias force member to deflect and thereby accommodate differently sized probes. The bias force member also typically applies a force to an ultrasound probe disposed in the clamp when the first and second body members are in a closed position. That is, in addition to accommodating differently sized ultrasound probes, the bias force member also securely hold the probe within the clamp. This may reduce or substantially eliminate relative movement/wobble between the supported ultrasound probe and the clamp body. In a further arrangement, two or more bias force members may be disposed on the inside surfaces of the first and/or second body members. Utilization of separate bias force members may allow for more conformal engagement with a supported ultrasound probe.

As utilized herein, the term bias force member includes, without limitation, resilient or elastic members (e.g., elastomeric blocks) disposed on the surfaces of the body members. Such bias force members may compress when the body members are closed relative to an ultrasound probe. In addition, such bias force members also include spring-type members (e.g., coiled springs and/or leaf springs). In any arrangement, a contact surface of the bias force members may be shaped to provide improved contact with an ultrasound probe disposed within the clamp. For instance, the bias force members may have a spherical or otherwise rounded contact surface that allows for improved contact between a probe and the bias force member. Further, a surface of the bias force member may include a gasket or other compressible material that allows for improved contact therebetween.

As the bias force member typically applies a force between the first and second body members when disposed about a portion of an ultrasound probe, a latch may be required to maintain the first and second members in a closed position. Any appropriate latch may be utilized. In one arrangement, the latch includes a male pin on one of the first and second body members that may be disposed within a female recess on the other of the first and second body members. In a further arrangement, the first and second body members may move axially relative to one another to allow the pin to be engaged within the recess. Further, such a pin may include a spring-loaded retention ball that is adapted to mate with an indention associated with the female recess. Such a spring-loaded retention ball may reduce or prevent unintended opening of the first and second body members.

The first and second body members may be concave members (e.g., half cylindrical members). In such an arrangement, the first and second body members may at least partially define a bore that is sized to receive an ultrasound probe. In such an arrangement, the bias force member(s) may be extend into the bore defined by the first and second body members. In any arrangement, the first and second body members may be pivotally connected. For instance, the first and second body members may be connected utilizing one or more hinge pins.

The mounting element associated with the surface of the clamp may be any element that allows the clamp to be interconnected to a desired positioning device. For instance, one or more apertures may be formed in a surface of one or both body members that allow the clamp to be physically connected (e.g., bolted) to a positioning device. Alternatively, the mounting element may be connectable to, for example, an end portion of the clamp body in order to mount the clamp body and/or a supported ultrasound probe to a positioning device.

According to another aspect, the device for supporting and rotating an ultrasound probe about a desired axis is provided. The device includes a disk having a first surface that is adapted to be rotatively mounted to a positioning device. A probe holding device is also provided for receiving a portion of an ultrasound probe. A connecting element is utilized to connect the probe holding device to a second surface of the disk. This connecting device may be adjustable to permit the selective positioning of a central axis of a receiving bore of the holding device relative to a rotational axis of the disk. It will be appreciated that often, a handle portion of an ultrasound probe, which may be disposed within the receiving bore, may be offset from an insertion portion or acquisition tip of the ultrasound probe. In this regard, it is desirable that the tip/acquisition portion of the probe rotate about a common axis with the disk. That is, during image acquisition, it is desirable that the acquisition tip of the probe rotate about a fixed axis to reduce registration error.

In a further arrangement, an outer periphery of the disk includes a plurality of notches. The device may further include a spring-loaded pawl for engaging the notches. In this regard, a user may, for example, manually turn the disk until the pawl engages a notch on the periphery of the disk. Images may then be acquired. The user may then turn the disk until the pawl engages the next notch. In this regard, the notches may be disposed at an even spacing about the periphery of the disk.

According to another aspect, a method for interfacing an ultrasound probe is provided. The method includes disposing a handle portion of an ultrasound probe between first and second body members of a clamp device while the body members are in at least partially open position. Once so disposed, the first and second body members may be moved to a closed position. In conjunction with moving the body members to the closed position, a bias force member may be compressed between the ultrasound probe and at least one of the first and second body members. Accordingly, the first and second body members may be latched together to secure the probe therebetween.

The method may further include attaching the clamp device to a positioning device. Such a positioning device may be operative to rotate the probe around at least one fixed axis. In this regard, the method may further include aligning and acquisition portion of the probe with a rotational axis of the positioning device. Such alignment may require offsetting the handle portion from the rotational axis of the positioning device.

BRIEF DESCRIPTION OF THE DRAWINGS

FIG. 2b illustrates a 3-D volume image generated from the two dimensional images of FIG. 2a.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging, it should be expressly understood that aspects of the present invention may be applicable to other medical imaging applications. In this regard, the following description is presented for purposes of illustration and description.

Disclosed herein are systems and methods that facilitate obtaining medical images and/or performing medical procedures. More specifically, a medical imaging device holder (i.e., holding device or cradle) is provided that is adapted to securely support multiple differently configured ultrasound probes. Further, a simplified rotational mechanism is provided.

The probe cradle may be interfaced with the rotational mechanism such that a supported probe may be rotated about a fixed axis. In this regard, multiple images may be obtained from the supported probe in different angular positions for 3-D image generation. As the probe is securely supported by the holding device, there may be little or no probe movement, other than about the fixed axis of rotation, between successive images. Accordingly, successive images may more easily be registered together. In other instances, the holding device may be utilized to securely position a probe relative to a tissue area of interest while a medical instrument is guided to the area of interest.

Figure 1:
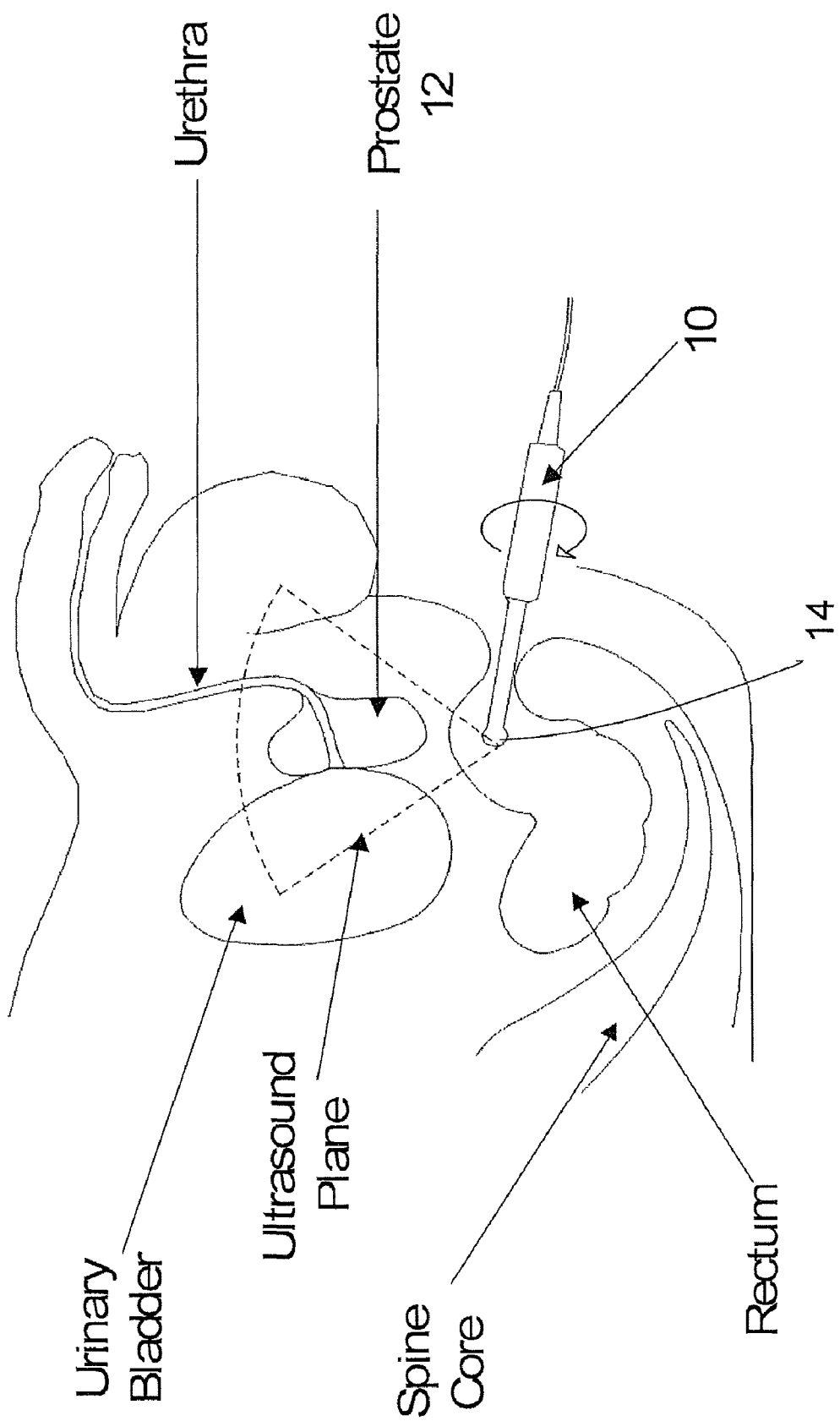
FIG. 1 shows a cross-sectional view of a trans-rectal ultrasound imaging system as applied to perform prostate imaging.
Figure 2A:
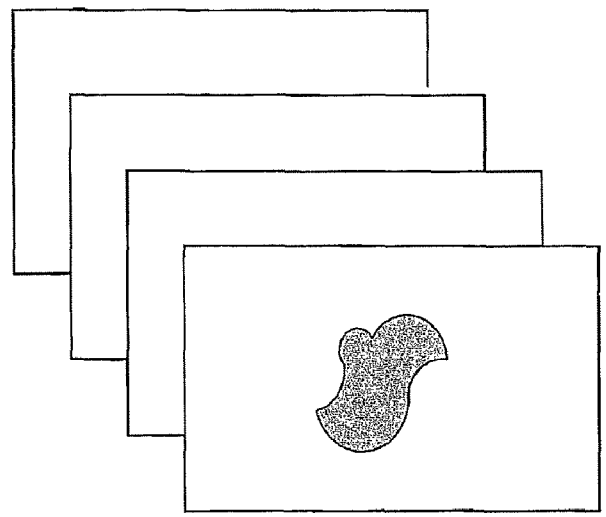
FIG. 2a illustrates two-dimensional images generated by the TRUS of FIG. 1.
Figure 2B:
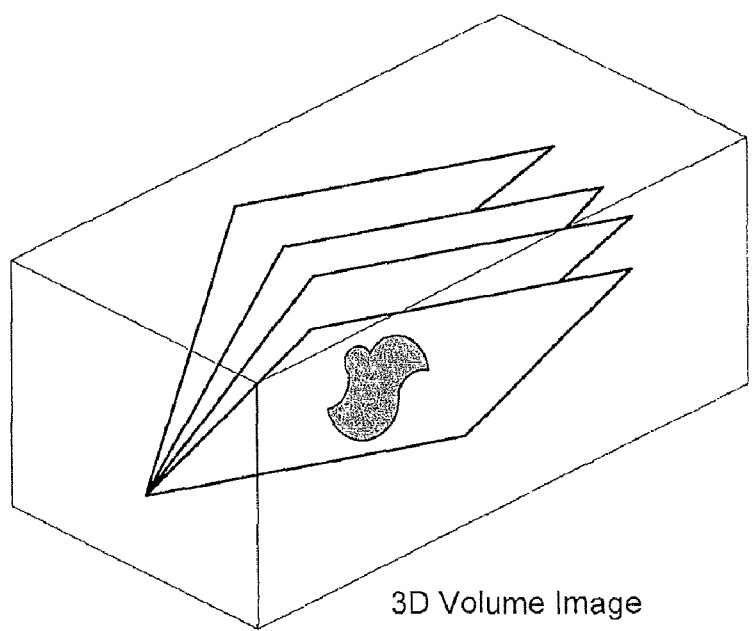

FIG. 1 illustrates a transrectal ultrasound probe being utilized to obtain a plurality of two-dimensional ultrasound images of the prostate 12. As shown, the probe 10 may be operative to automatically scan an area of interest. In such an arrangement, a user may rotate the acquisition end 14 of the ultrasound probe 10 over an area of interest. Accordingly, the probe 10 may acquire plurality of individual images while being rotated over the area of interest. See FIGS. 2A-B. Each of these individual images may be represented as a two-dimensional image. See FIG. 2A. Initially, such images may be in a polar coordinate system. In such an instance, it may be beneficial for processing to translate these images into a rectangular coordinate system. In any case, the two-dimensional images may be combined to generate a 3-D image. See FIG. 2B.

As shown in FIG. 1, the ultrasound probe 10 is a side-fire probe that generates ultrasound waves out of the side surface. However, it will be appreciated that end-fire scan probe may be utilized as well. In any arrangement, the probe 10 may also include a biopsy gun (not shown) that may be attached to the probe. Such a biopsy gun may include a spring driven needle that is operative to obtain a core from desired area within the prostate. In this regard, it may be desirable to generate an image of the prostate 12 while the probe 10 remains positioned relative to the prostate. If there is little or no movement between acquisition of the images and generation of the 3D image, the biopsy gun may be positioned to obtain a biopsy (or perform other procedures) of an area of interest within the prostate 12. However, manual manipulation of the probe 10 often results in relative movement between the probe and the prostate 12 between subsequent images and/or as a biopsy device is guided toward an area of interest.

Accordingly, for imaging is desirable that relative movement (e.g., wobble) between the probe 10 and the prostrate 12 be minimized (i.e., other than rotational movement of the probe about a fixed axis for image acquisition). Further, it is often desirable that the probe remains fixed relative to the prostrate 12 during biopsy or other treatment procedures such that desired tissue locations may be accurately targeted. To achieve such fixed positioning of the probe, it is often desirable to interface the probe 10 with a positioning device that maintains the probe 10 in a fixed relative position to the prostate. In order to utilize such a probe 10 with such a positioning device, it is necessary to secure the probe 10 to the device. That is, an interface between the probe and positioning device is required.

Figure 3:
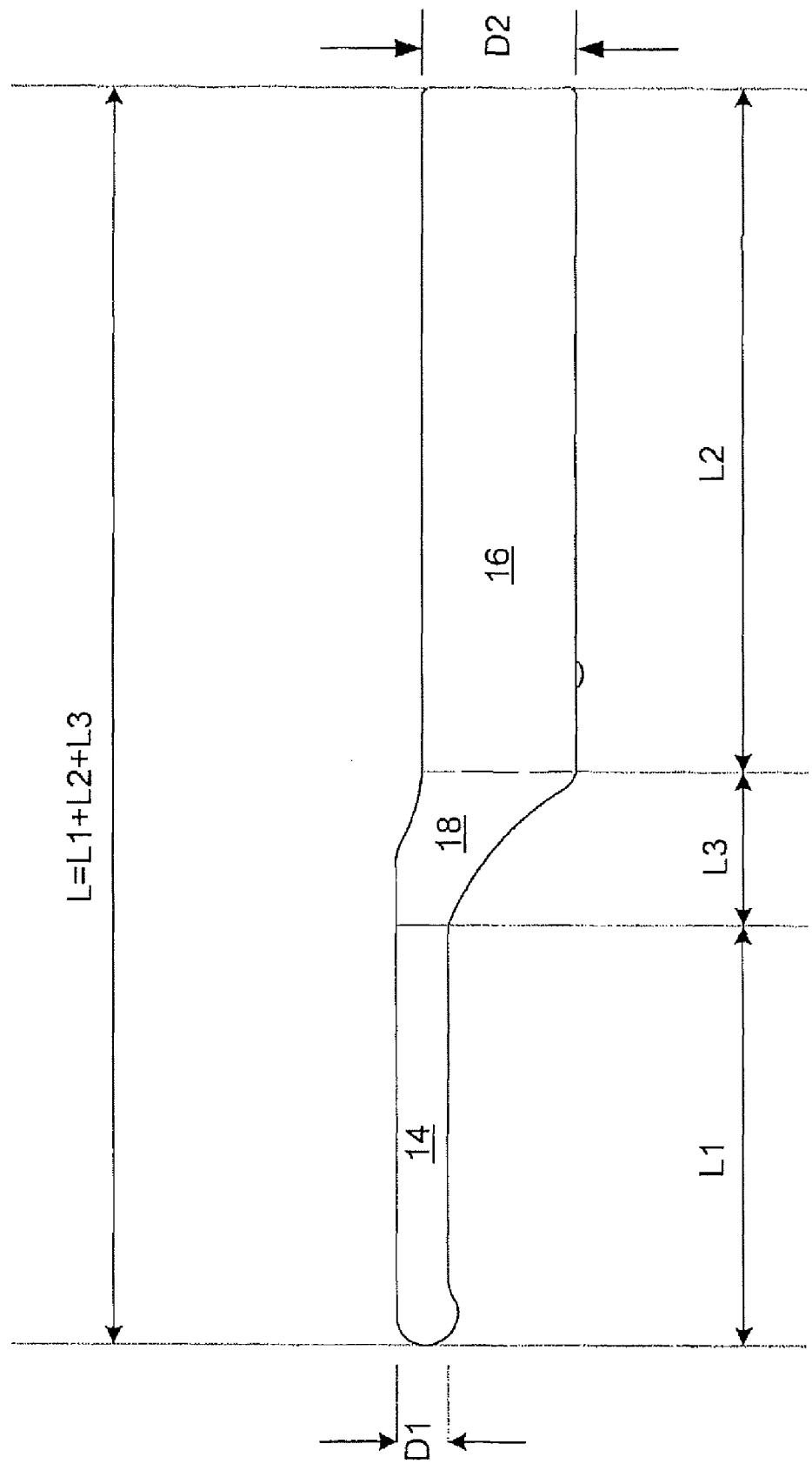
FIG. 3 illustrates an exemplary ultrasound probe.

Complicating the interfacing of an ultrasound probe with a positioning device is the fact that probes made by different probe manufacturers have different dimensions. For instance, FIG. 3 illustrates an exemplary TRUS probe 10. As shown, the probe includes an insertion end 14 having a first length $L_1$ (i.e., insertion length) and a first diameter $D_1$ (i.e., insertion diameter). The probe 10 also includes a handle 16 having a second length $L_2$ (i.e., a holding length) and a second diameter $D_2$. Further, the probe may have a transition 18 between the insertion end 14 and handle 16. In the present embodiment, the overall length of the probe 10 is defined by the combined lengths of these components, 14, 16 and 18.

However, the dimensions (e.g., lengths and/or diameters) of any or all of these components 14, 16 and 18 may vary between probes of different manufactures. Further, these components may be tapered and/or set at an angle to one another. Therefore, to interface different probes to a common positioning device requires either individual probe interfaces (i.e., probe holders) for individual probes, or, a probe holder that is operative to securely hold differently configured probes. Accordingly, provided herein is a universal probe holding device that may be securely connected to a positioning device, where the holding device can securely hold differently configured probes.

While different probes may have different dimensions, it is recognized that probes produced for a common purpose (e.g., TRUS probes) are generally similar in size and shape. Accordingly, a holding device may need to accommodate relatively small differences in, for example, handle diameter and/or overall length to permit the device to securely support probes of different manufacturers.

Figure 4A:
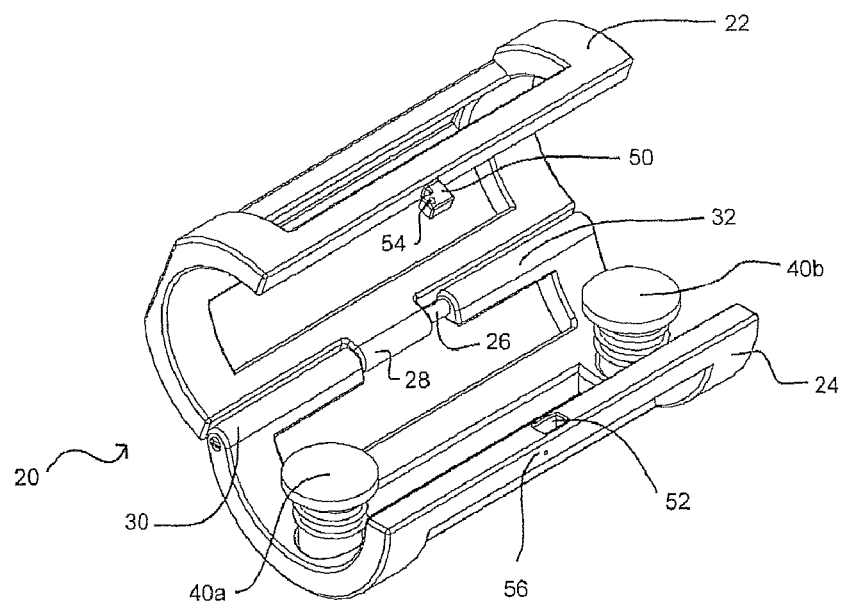
FIGS. 4A and 4B illustrate top and bottom perspective views, respectively, of a probe holding device.
Figure 4B:
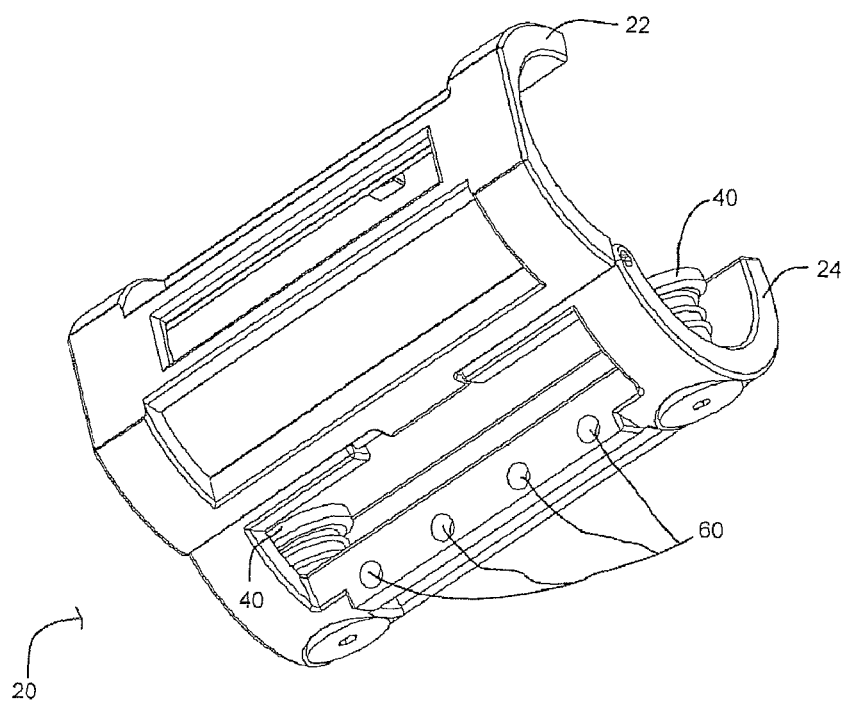

FIGS. 4A and 4B illustrates top and bottom perspective views of a holding device 20 that may be utilized to hold differently configured probes. As shown, the device 10 generally defines a clamp that is designed to open and close about a handle portion of an ultrasound probe. In this regard, the device 20 includes an upper body member 22 and a lower body member 24 that are connected using a hinge. In this regard, the upper body member 22 and lower body member 24 are operative to move relative to one another (e.g., pivot) about a hinge axis, that in the current embodiment is defined by a hinge pin 26. More specifically, the lower body member 24 includes first and second clevises 30, 32 and the upper body member 22 includes a single clevis 28 that is disposed between the first and second clevises 30, 32 of the lower body member 24. As shown, the clevises 28, 30,32 receive the hinge pin 26 through a plurality of axially aligned apertures in the clevises.

The upper and lower body members 22, 24 are generally defined as concave members where a recessed surface of each body member 22, 24 is generally aligned (e.g., parallel) with the axis defined by the hinge pin 26. In the present embodiment, the upper and lower body members and 22, 24 are generally C-shaped when viewed from an end. See FIGS. 5A and 5B. In this regard, the upper and lower body members 22, 24 may define a bore therebetween when in a closed position. This bore is adapted to receive an ultrasound probe. In this regard, a body/handle 16 of an ultrasound probe 10 may be disposed between the upper and lower body members 22, 24 of the device 20 while those members are an open position. See FIG. 6A. Once an ultrasound probe 10 is disposed between the upper and lower body members 22, 24 of the holding device 20, those members may be moved to a closed position relative to one another. See FIG. 6B. In the closed position, the probe 10 is secured within the bore that is defined by the first and second body members 22, 24.

In order to accommodate differently sized probes, and it is necessary that the inside surface of the holding device 20 at least partially conform to probes having different dimensions. In this regard, the device 20 may be utilized with a variety of differently configured ultrasound probes. Referring again to FIGS. 4A and 4B, it will be noted that the inside surface of at least one of the body members 22, 24 of the device 20 includes a resilient member adapted to conform to the surface of the probe 10 when the first and second body members 22, 24 are closed.

In this particular embodiment, the resilient member is formed of a bias force member that is adapted to engage a surface of the probe disposed within the bore of the device 20 and apply a force to the probe 10 which prevents relative movement between the probe 10 and the holding device 20. As shown, the present embodiment utilizes first and second bias force members, which are represented as spring-loaded pressure plates 40a, 40b (referred to as pressure plates 40 unless specifically identified). The pressure plates 40 are spring loaded such that when an ultrasound probe is disposed within the device and the device is closed (See FIG. 8), the pressure plates 40 are deflected towards the bottom of the lower body member 24 of the device 20 and exert a force between the probe 10 and the device 20.

Figure 5A:
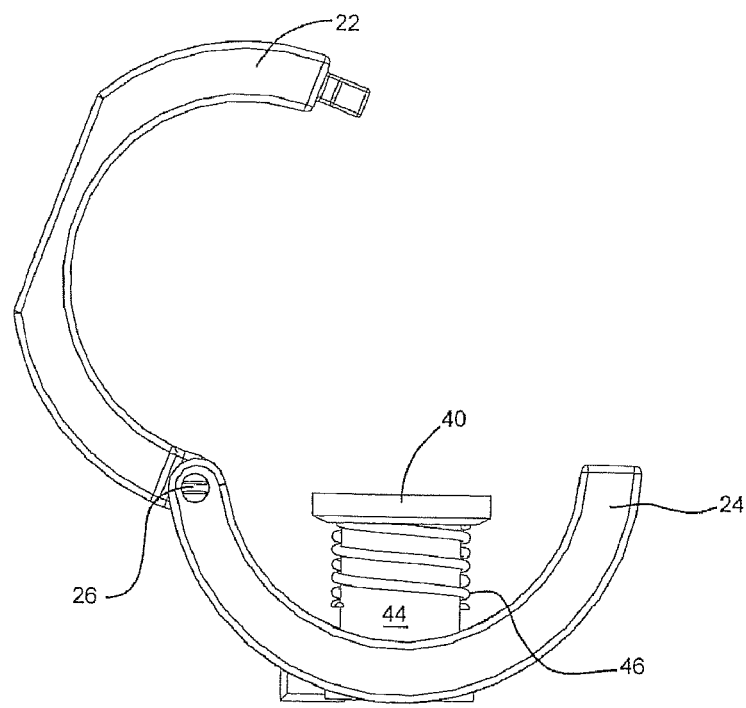
FIGS. 5A an 5B illustrate end views of a probe holding device in open and closed configurations, respectively.
Figure 5B:
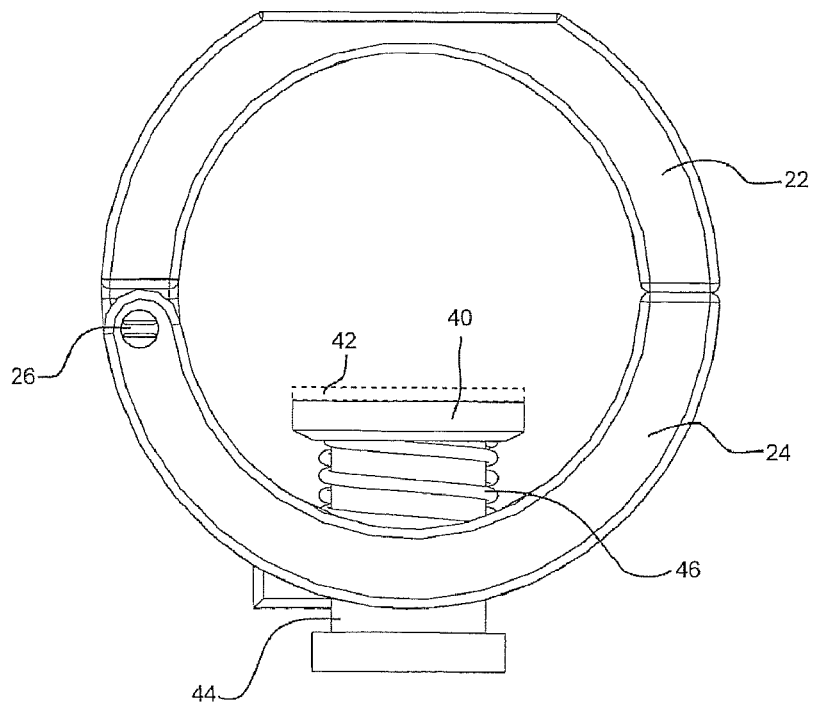
FIG. 5C illustrates an end view of the probe holding device with a compressible gasket.
FIG. 5D illustrates an end view of the probe holding device incorporating a lock release mechanism.
Figure 5C:
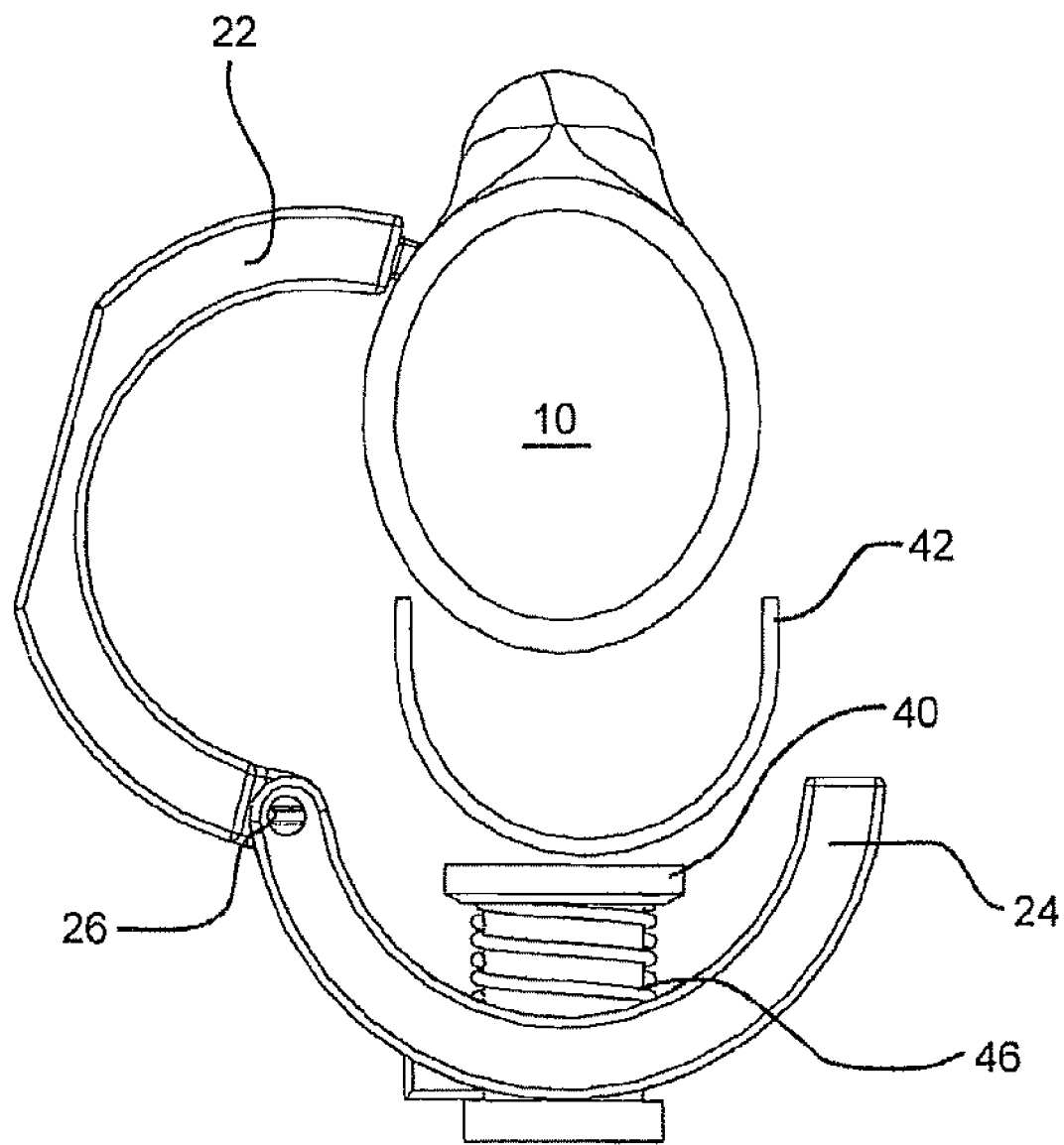
Figure 5D:
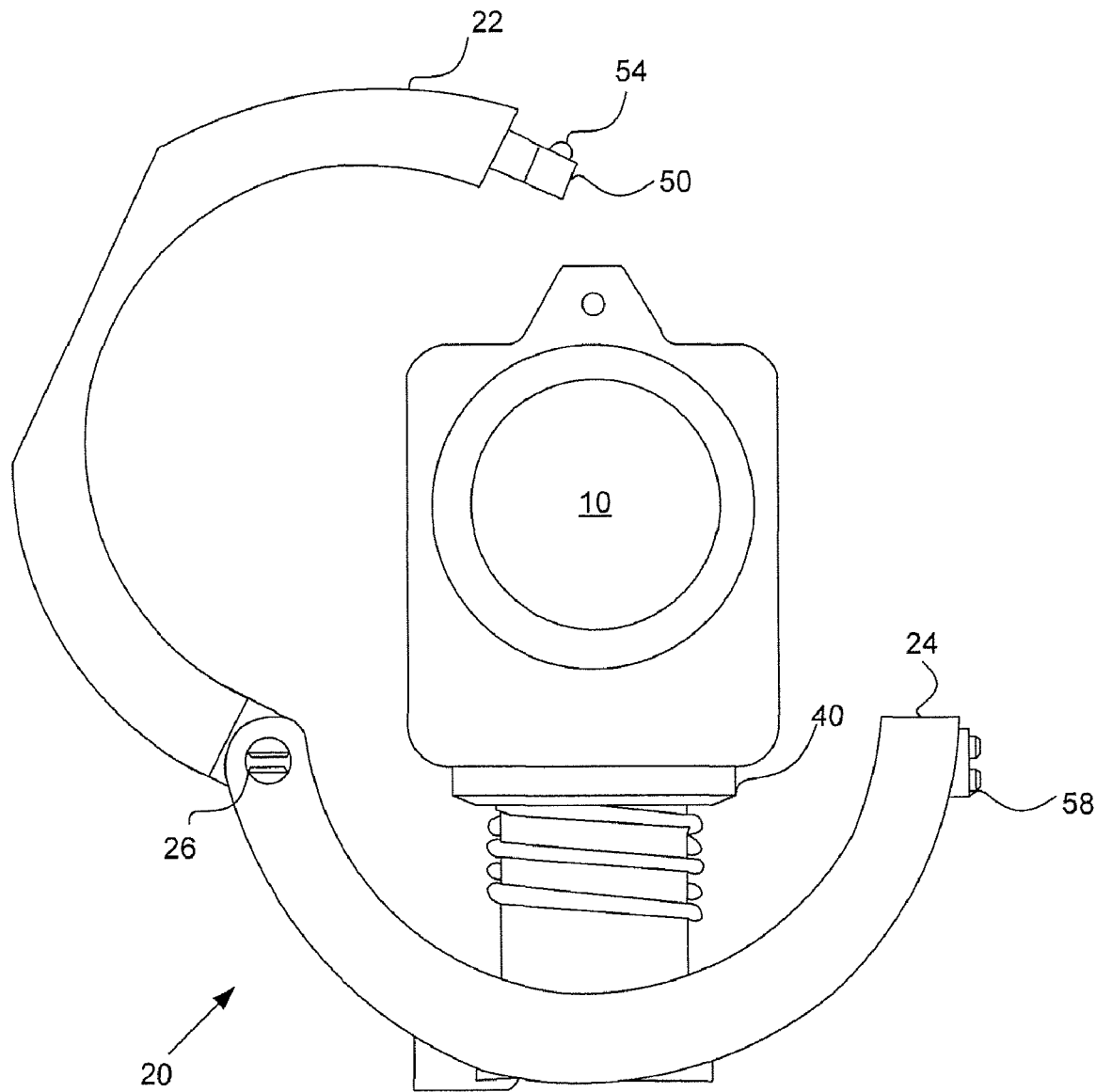

As shown, the pressure plates 40 in this particular embodiment, extend through a bottom surface of the lower member 24 when compressed. See FIGS. 5A-D. However, it will be appreciated that other embodiments may be provided where the bias force members do not extend through the bottom member. The pressure plates 40 include an upper contact surface 42 that is adapted to engage a probe disposed within the bore of the device 10. This upper contact surface 42 may be rounded and/or partially spherical to provide better contact with the probe. Further, the contact surface 42 may be covered by a resilient material (e.g., a gasket, rubber, elastomeric material or other compressible material) to improve the contact between the bias force member 40 and a probe 10. This compressible material may have any shape that allows for conformance with a probe 10 dispose within the holding device 20. For instance, as shown in FIG. 5C, the gasket may be U-shaped to conform with an outside surface of the probe 10. Of note, other inside surfaces of the upper and lower body members 22, 24 may also include a resilient/compressible material for purposes of providing better contact between the device 20 and a probe 10.

A spring 46 is disposed around outside surface of a body portion 44 of the pressure plate 40. This spring 46 is disposed between an upper lip on the pressure plate 40 and the bottom inside surface of the lower body member 24. Compression of this spring allows the body portion 44 of the pressure plate 40 to move through the lower body member 24. It should be noted that while first and second bias force members 40a, 40b are utilized in the current embodiment, more or fewer bias force members may be utilized. Further, such bias force members may take different forms. For instance, a leaf spring may extend between the first and second ends of one or both of them members to provide a conformal fit with a probe disposed within the device 20.

In any embodiment, the bias force members may be deflected when an ultrasound probe is disposed within the device 20. That is, the bias force members may deflect to accommodate a probe. However, the bias force members will resist such deflection and thereby apply a force between the probe and the device 20 when the upper and lower body members 22, 24 are closed. Such deflection and applied force allows differently sized probes to be secured within the device 20. Further, such applied force allows for holding a probe 10 with little or no relative movement between the device 20 and the probe. That is, such an arrangement allows for reducing wobble between the probe 10 and the holding device 20.

As noted above, the top and bottom body members 22, 24 are operative to move relative to one another in order to accommodate an ultrasound probe therebetween. Further, one or both body members 22, 24 may include bias force members, e.g., pressure plates, that apply a force between a received probe and the inside surfaces of the device 20. Accordingly, it is necessary to provide a lock mechanism to maintain the upper and lower body members 22, 24 in a closed position when a probe 10 is disposed within the device 20.

Figure 7A:
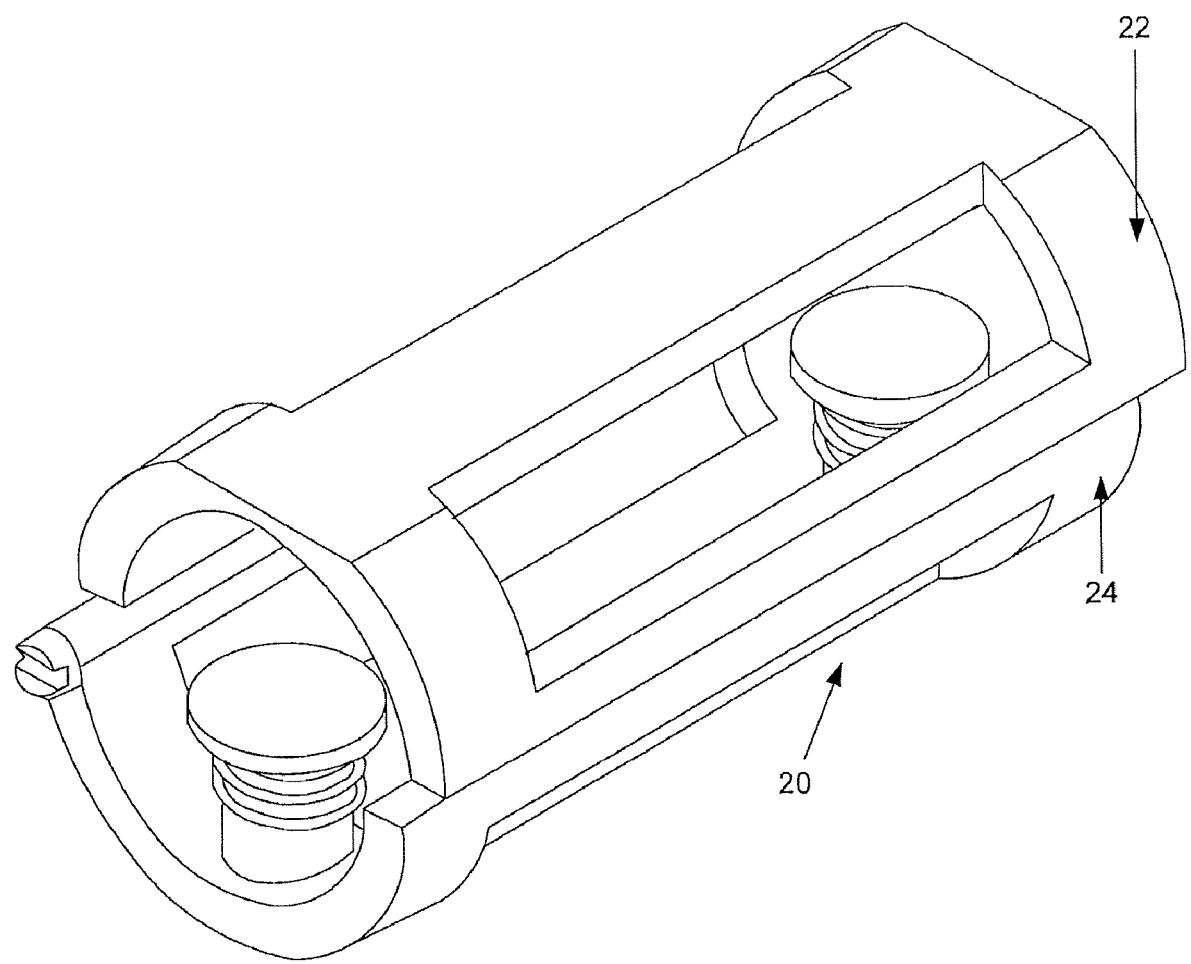
FIGS. 7A and 7B illustrate axial movement between upper and lower body members of the device.
Figure 7B:
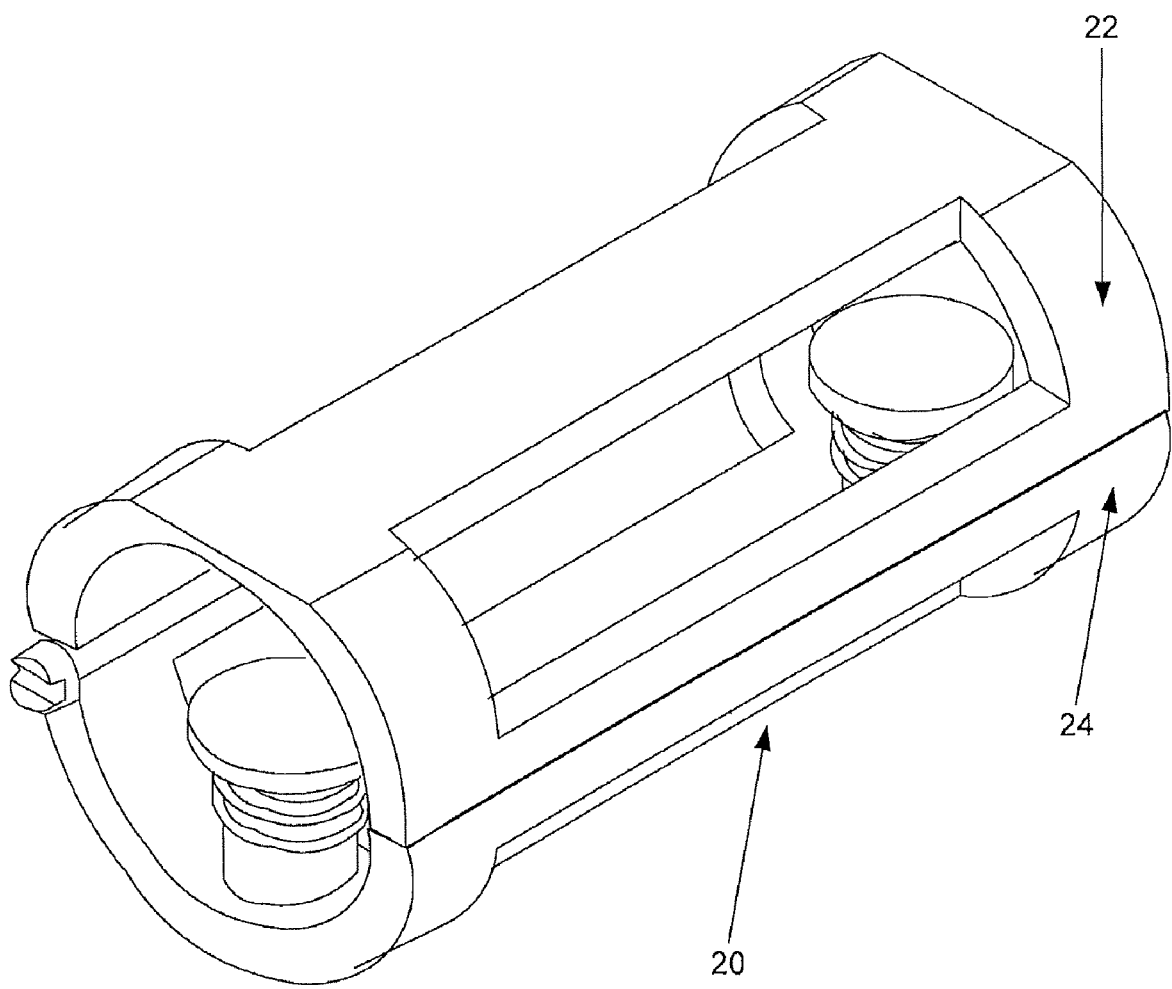

The present embodiment of the device utilizes a slide lock arrangement. As shown in FIGS. 4A, the clevis 28 of the upper body member 22 is narrower than the space between the clevises 30, 32 of the body member 24. This allows the upper body member 22 to move axially along the hinge pin 26 between the clevises 30, 32 of the lower body member 24. That is, the upper and lower body members of the device 20 are permitted to move to axially relative to one another. In this regard, a male connecting pin 50 on one of the body members 22, 24 may be selectively received within a mating female recess 52 on the other body member 22, 24. In the present embodiment, an L-shaped connecting pin 50 is attached to the free lateral edge of the upper body member 22. The corresponding edge of the lower body member 24 includes a recess 52 that opens to an L-shaped cavity. The connecting pin 50 may be disposed within the recess 52 and the upper body member 22 may be advanced axially relative to the lower body member. See FIGS. 7A and 7B. In such an arrangement, the L-shaped pin 50 may be disposed beneath a lip of the aperture 52 by sliding the upper body member 22 relative to the lower body member 24.

The connecting pin 50 includes a spring loaded retention ball 54 on its front face. See FIGS. 4A and 5D. When the upper body member 22 of the device 20 is closed relative to the lower body member and the connecting pin 50 is disposed within the recess/aperture 52, the retention ball 54 engages an indentation 56 or aperture within the cavity that receives the connecting pin 50. This allows for locking the upper and lower members 22, 24 in the position shown in FIG. 7B. That is, the spring loaded retention ball 54 provides a resistance to being retracted from the indentation 56 and thereby prevents unintentional opening of the device. In order to open the device 20, the upper body member 22 is retracted with either a force that is sufficient to overcome the spring loading of the retention ball, which then disengages from the indentation 56 and allows the connecting pin 50 to be withdrawn from the cavity. Alternatively, the lower body member 24 may have a release mechanism 58. See FIG. 5D. By depressing the release mechanism 58, the retention ball 54 may be disengaged from the indention 56 and thereby facilitate the retraction of the connecting pin 50 from the recess 52. However, it will be appreciated that other locking mechanisms may be utilized to maintain the upper and lower members 22, 24 in a closed position and such mechanisms are within the scope of the present invention.

FIG. 4B illustrates a bottom perspective view of the device 10. As shown, on the outside surface of the lower body member 24, there is a plurality of mounting holes 60 that forms one embodiment of a mounting element for the device 20. These mounting holes 60 may be utilized to mount the device to a positioning device such as, for example, a robotic positioning device. However, it should be noted that other arrangements for mounting the device 20 to a positioning device are possible and considered within the scope of the invention.

Figure 8:
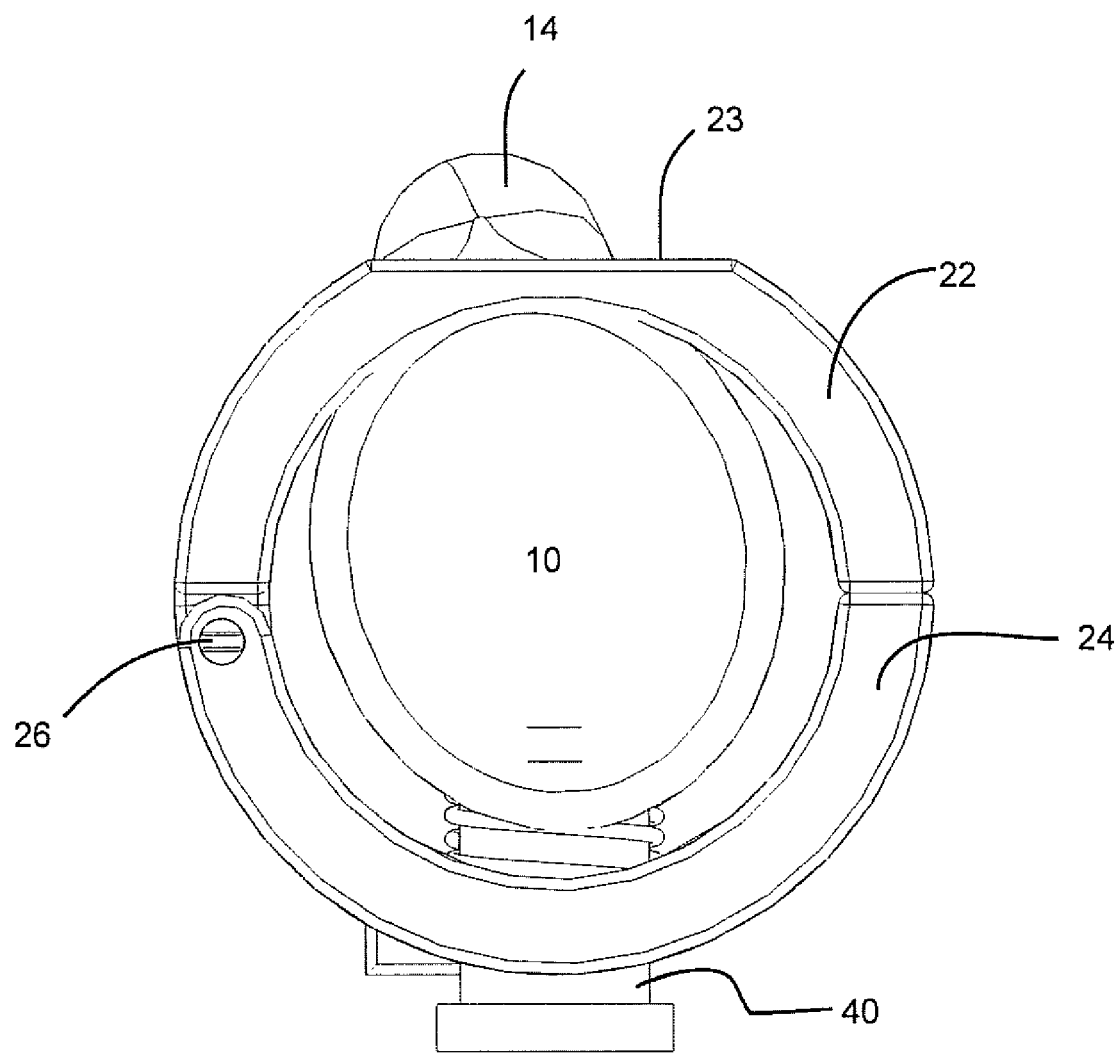
FIG. 8 illustrates a rear end view of a probe disposed within a probe holding device.
Figure 9:
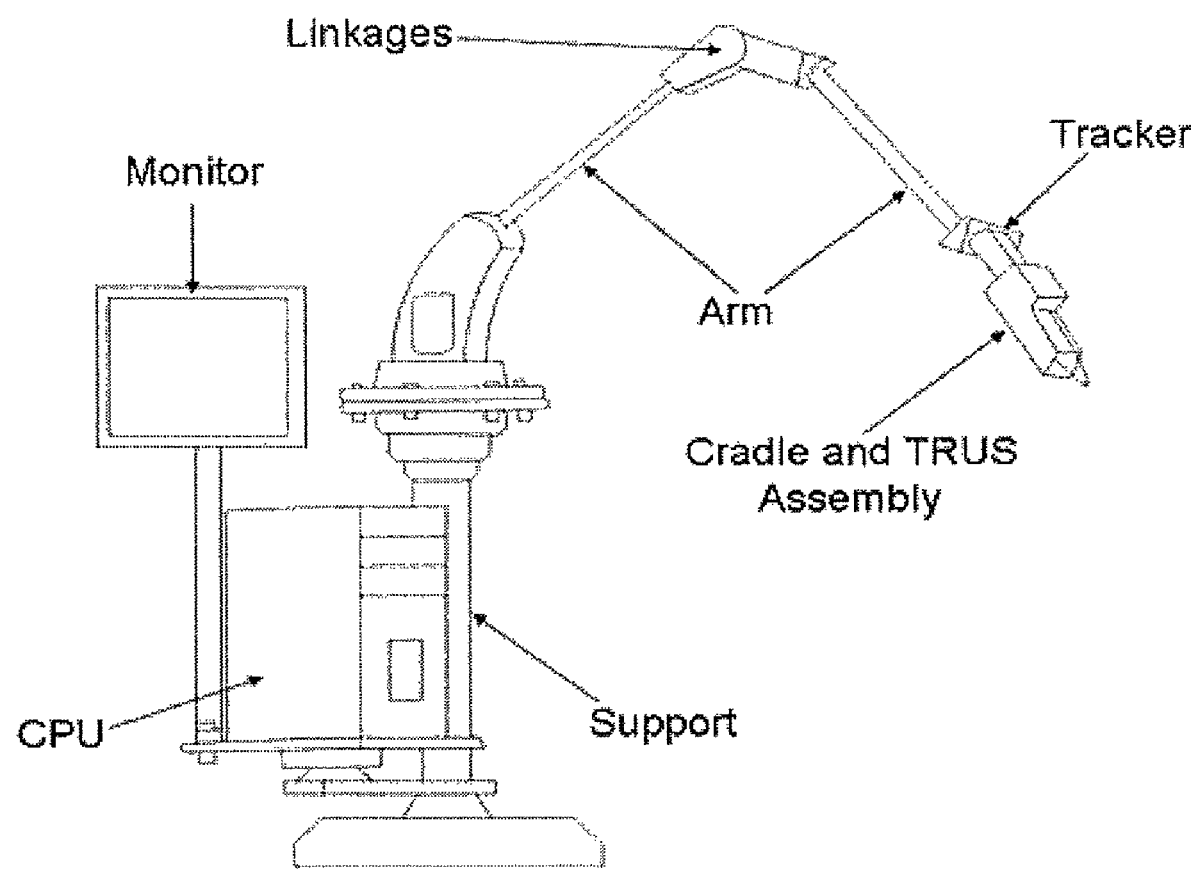
FIG. 9 illustrates one embodiment of a positioning device.

Of note, a top edge 23 of the upper member 24 may be shaped in a manner that permits a biopsy needle or other treatment element to access the insertion end 14 of the probe 10. As illustrated by FIGS. 5A, 5B and 8, the top edge 23 of the upper member is flattened to permit access past the holding device 20 to the insertion end of the probe 10. This flattened section 23 may also be used to mount an emergency switch for immediate release of the TRUS probe from the rectum of the patient and to immediately stop any automatic motion. FIG. 9 illustrates one embodiment of a robotic actuator (e.g., positioning device) to which the holding device 20 may be connected. However, it will be appreciated that any robotic actuator may be utilized, and the illustrated robotic actuator is provided by way of illustration and not by limitation. What is important is that the holding device 20 may be affixed to a positioning device and that the holding device 20 accommodates ultrasound probes having different physical configurations. In this regard, the holding device may receive and securely hold ultrasound probes from various different manufacturers such that differently configured probes may be utilized with a single positioning device. Further, the probe held by the device 20 is secured by the resilient and/or bias force members disposed within the clamp, which prevents wobble (e.g., relative movement between the holding device 20 and probe 10).

During image acquisition, it is typical to insert the insertion end of an ultrasound probe relative to a tissue area of interest (e.g., the prostrate). Once so positioned, the probe may be rotated around the axis of its tip (e.g., for an end-fire probe) while a plurality of 2-D images are obtained for use in generating a 3-D image. Preferably, the images are acquired at equal angular offsets in order to provide an improved 3-D image.

Figure 6A:
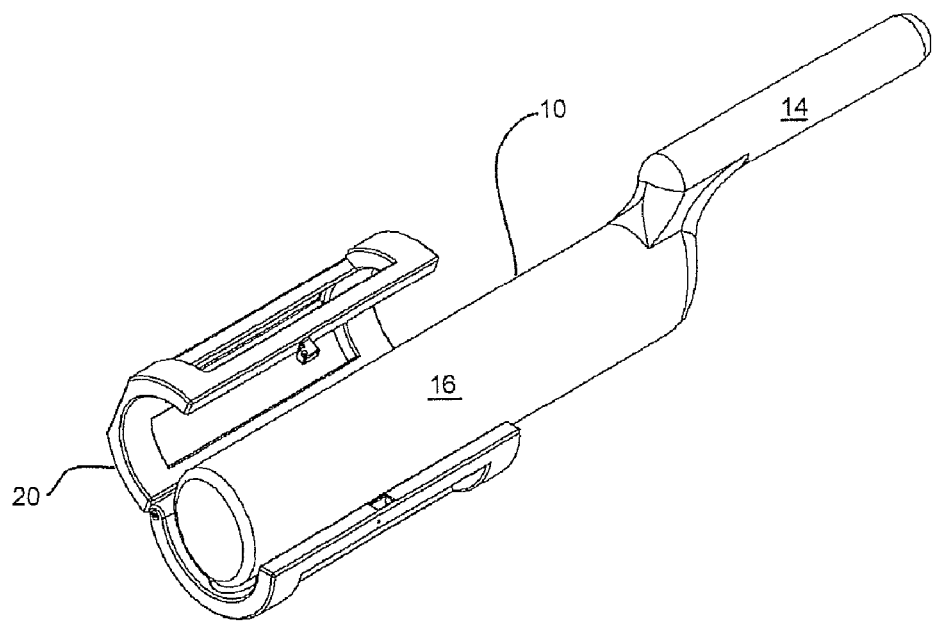
FIGS. 6A an 6B illustrate end an ultrasound probe disposed in a probe holding device in open and closed configurations, respectively.
Figure 6B:
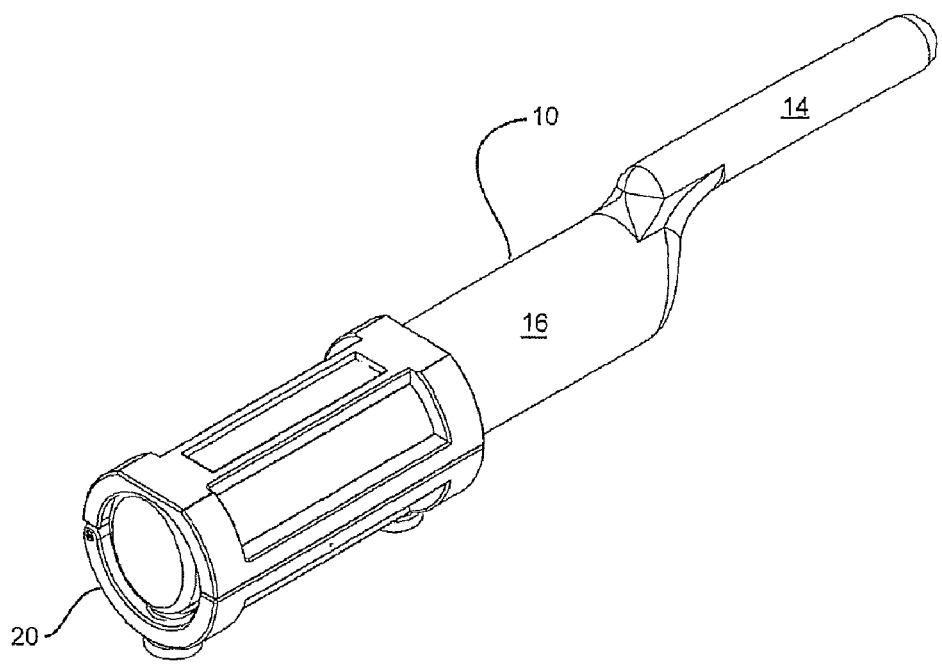

In this regard, it is desirable that the probe tip and typically the insertion end of the probe rotate around a fixed axis. However, as illustrated by FIGS. 3, 6A and 6B, it is noted that in many instances the axis of the insertion end 14 of the probe 10 is offset from the axis of the handle 16 of the probe 10. Further, when the probe 10 is disposed within the holding device 20, the axis of the insertion end 14 of the probe is offset from the central axis of the holding device 20. In order to effectively rotate the probe 10 around the insertion/tip axis, it may be necessary to rotate the holding device 20 and, hence, the handle 16 of the probe 10 about an offset axis. That is, it may be necessary to correct for axial misalignment of the probe 10.

Figure 10:
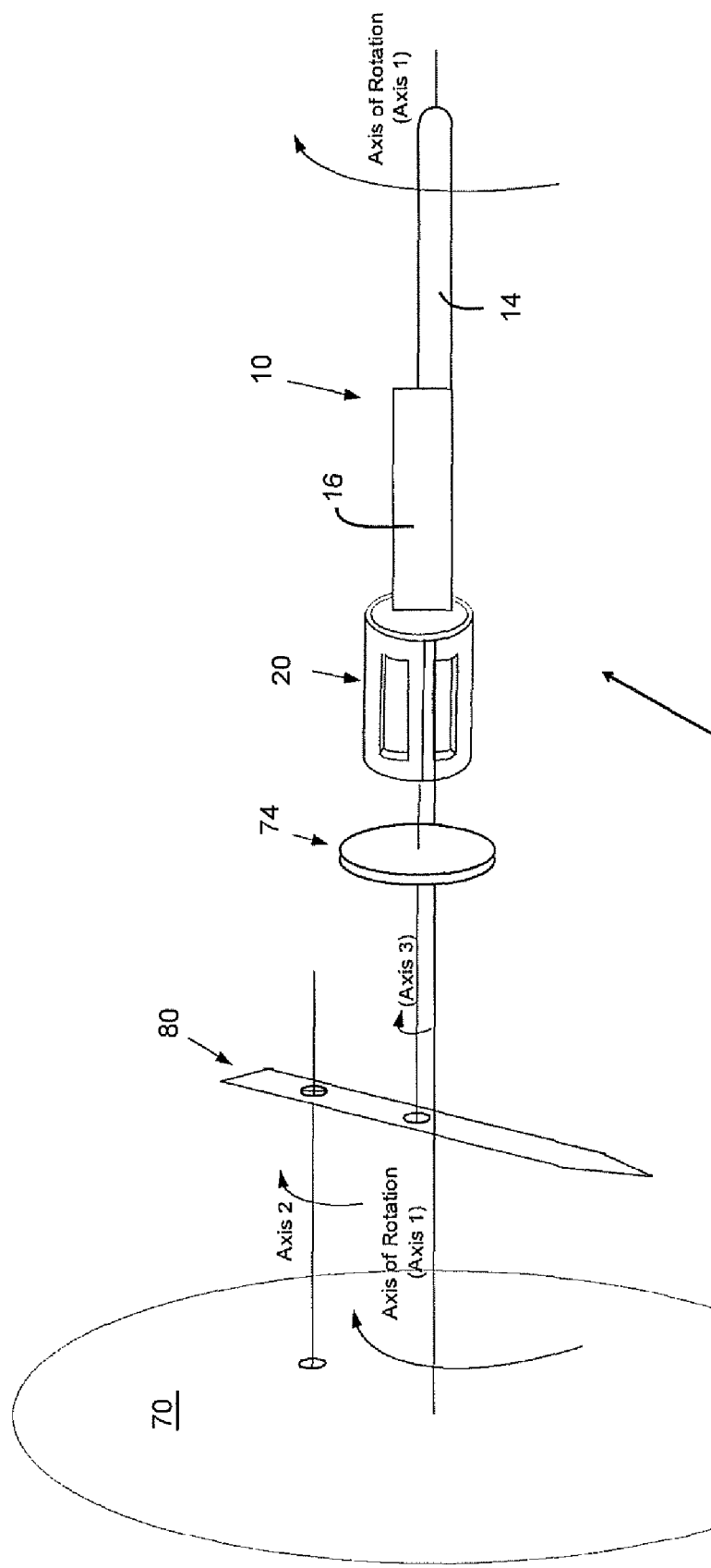
FIG. 10 illustrates another embodiment of a positioning device.

Accordingly, FIG. 10 provides an illustration of a device that allows correcting the misalignment of the axes of the probe 10 such that the rotation takes place with respect to the insertion end/tip of the probe 10. As shown, the assembly 100 allows for correcting the misalignment of the axis of the insertion end of the probe (axis 1) and the axis of the handle/holding device (axis 3). Generally, the assembly 100 includes a rotating disk 70, which may be rotatively coupled to a positioning device and/or robotic arm (e.g., of FIG. 9). The axis of rotation of the insertion end of the probe 10 is aligned with the axis of rotation of the rotating disk 70 (i.e, axis 1).

Figure 11:
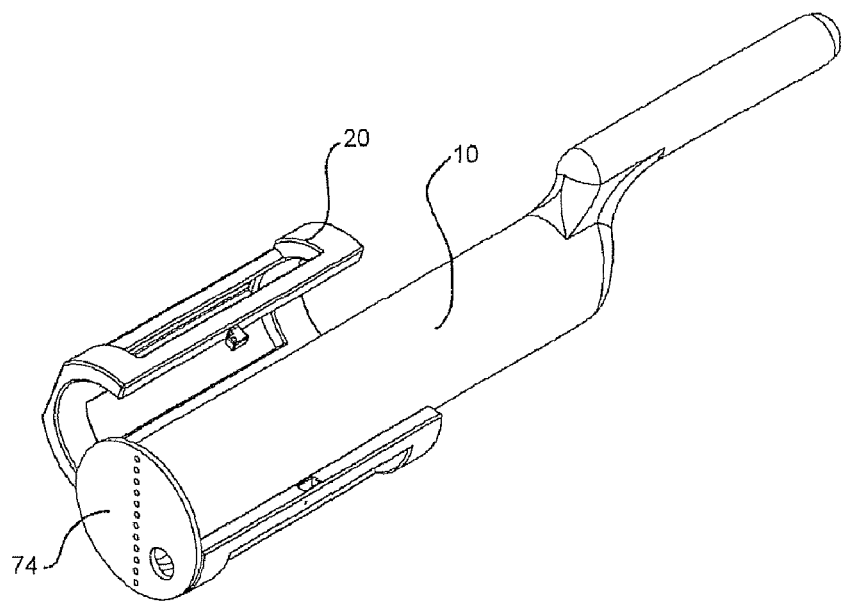
FIG. 11 illustrate an attachment element for attaching a probe holding device to the positioning device of FIG. 10.

To permit alignment of the insertion end 14 of the probe 10 with the rotational axis of the disk 70, the holding device 20 must be connected to the disk 70 at a distance from the axis of rotation (axis 1) to account for the offset between the insertion end 14 of the probe and the probe handle 16 and/or central axis of the holding device 20. As shown in FIGS. 10 and 11, the holding device 20 is connected to an axis alignment tool 74. As shown, the axis alignment tool 74 interconnects to the probe holding device 20. The axis alignment tool forms a second embodiment of a mounting element for the holding device 20. The axis alignment tool 74 is adapted to be mounted to the parallel axis offset tool 80.

The parallel axis offset tool 80 is interconnectable to the disk 70 at a position (axis 2) that is offset from the axis of rotation (axis 1) of the disk 70. By adjusting the angular position of the parallel axis offset tool 80 relative to its connection point (i.e., axis 2) with the disk 70, the axis of the insertion end 14 of the probe may be aligned with the rotational axis of the disk 70. That is, the parallel axis offset tool 80 will be rotated about axis 2 and the axis alignment tool may be displaced such that the insertion end axis is substantially aligned with the axis of rotation (i.e, axis 1).

As may be appreciated, in most instances of manual image sampling, a user is not able to uniformly control the angular rotation of the probe between successive samples. That is, manual acquisition of ultrasound data suffers from the drawback of irregular sampling rates and such irregularly sampled data may cause bad image quality when reconstructed into a 3-D image. The design of the assembly 100 of FIG. 10 may also be adapted to allow for uniform sampling during manual rotation of the probe 10.

Figure 12:
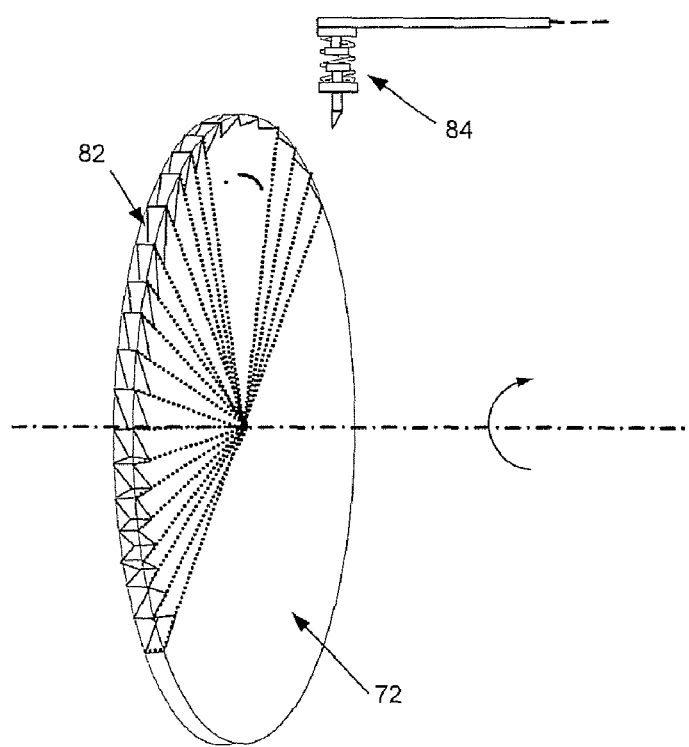
FIG. 12 illustrates a notched disk that allows the positioning device of FIG. 10 to be manually rotated while providing constant angular rotation for imaging purposes.

The assembly shown in FIG. 12 provides a mechanism for manual rotation of a TRUS probe at regularly spaced acquisition angles. The saw-tooth disk 72, which may be incorporated into a positioning mechanism (e.g., see FIGS. 9 and 10), has uniformly spaced notches 82 about its periphery. Further the saw-toothed disk 72 may include a combination of discs (e.g., stacked) with different sampling angles. As a user rotates the assembly, a spring-loaded pin or pawl 84 engages the notches. Accordingly, images may be sampled at each notch. This ensures that 2-D images are acquired at uniform sampling angles. It will be appreciated that the saw-toothed wheel may have notches defining various desired sampling rates such as 1°, 2°, 3°, resulting in a flexible, yet uniform manual sampling apparatus.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in similar or other embodiments and with various modifications required by the particular application(s) or use(s) of the present invention. It is intended that the appended claims be construed to include alternative embodiments to the extent permitted by the prior art.

What is claimed:

1. An apparatus for interfacing with an ultrasound probe, comprising:
    a clamp body for receiving a portion of an ultrasound probe, the clamp body including:
        a first body member;
        a second body member movably attached to the first body member, wherein the first and second body members are concave members and adapted to move between an open position and a closed position wherein concave surfaces of the first and second body members at least partially define a bore for receiving an ultrasound probe;
    at least one bias force member disposed on a surface of one of the first and second body members; and
    a mounting element associated with a surface of the clamp body, wherein the mounting element allows selective attachment of the clamp body to a positioning device.

2. The apparatus of claim 1, wherein the bias force member applies a force to an ultrasound probe disposed within the clamp when the first and second body members are in the closed position.

3. The apparatus of claim 2, further comprising:
    at least two bias force members, wherein the first and second bias force members are mounted to a common one of the first and second body members.

4. The apparatus of claim 2, wherein the bias force member comprises a spring loaded bias force member, wherein the spring loaded bias force member moves at least partially radially relative to a center axis of the clamp body.

5. The apparatus of claim 2, wherein a contact surface of the bias force member is at least partially rounded.

6. The apparatus of claim 2, wherein a contact surface of the bias force member further comprises a compressible element.

7. The apparatus of claim 1, further comprising:
    a latch for maintaining the first and second members in the closed position.

8. The apparatus of claim 7, wherein the latch comprises a male pin disposed on one of the first and second body members and a female recess on the other of the first and second body members.

9. The apparatus of claim 8, wherein the first and second body members are adapted to move axially in relation to a central axis of the clamp body to engage and disengage the male pin with the female aperture.

10. The apparatus of claim 8, wherein the male pin further comprises:
    a spring loaded retention ball adapted to mate with an indention associated with the female recess.

11. The apparatus of claim 1, wherein the first and second body members are pivotally connected using at least a first hinge pin.

12. The apparatus of claim 1, further comprising:
    a disk adapted to be rotatively mounted to a positioning device, wherein the clamp body is mounted to the disk.

13. The apparatus of claim 12, wherein the clamp body is mounted such that a central axis of the clamp body is offset from a rotational axis of the disk.

14. The apparatus of claim 12, wherein an outer periphery of the disk includes a plurality of notches.

15. The apparatus of claim 14, further comprising a pawl for engaging the notches.

16. An apparatus for interfacing with an ultrasound probe, comprising:
    a clamp body for receiving a portion of an ultrasound probe, the clamp body including:
        a first body member;
        a second body member movably attached to the first body member, wherein the first and second body members are adapted to move between an open position and a closed position;
    at least one bias force member disposed on a surface of one of the first and second body members;
    a latch for maintaining the first and second members in the closed position; and
    a mounting element associated with a surface of the clamp body, wherein the mounting element allows selective attachment of the clamp body to a positioning device.

17. The apparatus of claim 16, wherein the first and second body members are concave members, wherein concave surfaces of the first and second body members at least partially define a bore for receiving an ultrasound probe.

* * * * *